United States Patent [19]
Bartz et al.

[11] Patent Number: 5,714,446
[45] Date of Patent: Feb. 3, 1998

[54] SHAMPOO COMPOSITIONS WITH SILICONE AND CATIONIC SURFACTANT CONDITIONING AGENTS

[75] Inventors: Lisa Jo Bartz; James David Landgrebe; Robert Lee Wells, all of Cincinnati, Ohio

[73] Assignee: The Procter & Gamble Company, Cincinnati, Ohio

[21] Appl. No.: 385,228

[22] Filed: Feb. 8, 1995

Related U.S. Application Data

[63] Continuation of Ser. No. 260,619, Jun. 16, 1994, abandoned, which is a continuation of Ser. No. 74,700, Jun. 10, 1993, abandoned, which is a continuation of Ser. No. 852,363, Mar. 13, 1992, abandoned, which is a continuation of Ser. No. 622,705, Jan. 25, 1990, abandoned.

[51] Int. Cl.$^6$ ............... C11D 1/86; C11D 9/36; C11D 1/62; C11D 1/12
[52] U.S. Cl. ............... 510/119; 510/122; 510/123; 510/124; 510/125; 510/126; 510/127; 510/502; 510/499; 510/501; 510/504; 510/466
[58] Field of Search ............... 252/547, 174.15, 252/DIG. 13; 510/122, 123, 124, 125, 126, 127, 499, 501, 502, 504, 466

[56] References Cited

U.S. PATENT DOCUMENTS

| | | | |
|---|---|---|---|
| 2,826,551 | 3/1958 | Geen | 252/89 |
| 3,929,678 | 12/1975 | Laughlin et al. | 252/526 |
| 3,964,500 | 6/1976 | Drakoff | 132/7 |
| 3,969,500 | 7/1976 | Kennerley | 424/10 |
| 3,990,991 | 11/1976 | Gerstein | 252/542 |
| 4,009,256 | 2/1977 | Nowak et al. | 424/70 |
| 4,220,168 | 9/1980 | Newell | 132/7 |
| 4,264,457 | 4/1981 | Beeks et al. | 252/8.75 |
| 4,330,526 | 5/1982 | Watanabe et al. | 424/70 |
| 4,364,837 | 12/1982 | Pader | 252/173 |
| 4,374,125 | 2/1983 | Newell | 424/70 |
| 4,529,586 | 7/1985 | DeMarco et al. | 424/70 |
| 4,576,729 | 3/1986 | Paszek et al. | 252/106 |
| 4,597,962 | 7/1986 | Grollier et al. | 424/47 |
| 4,673,568 | 6/1987 | Grollier et al. | 424/47 |
| 4,704,272 | 11/1987 | Oh et al. | 424/70 |
| 4,707,293 | 11/1987 | Ferro | 252/174.17 |
| 4,710,314 | 12/1987 | Madrange et al. | 252/117 |
| 4,726,944 | 2/1988 | Osipow et al. | 424/70 |
| 4,728,457 | 3/1988 | Fieler et al. | 252/174.15 |
| 4,741,855 | 5/1988 | Grote et al. | 252/142 |
| 4,749,565 | 6/1988 | Grollier | 424/70 |
| 4,788,006 | 11/1988 | Bolich et al. | 252/550 |
| 4,842,850 | 6/1989 | Vu | 424/70 |
| 4,859,456 | 8/1989 | Marschner | 424/47 |
| 4,902,499 | 2/1990 | Bolich et al. | 424/70 |
| 4,906,459 | 3/1990 | Cobb et al. | 424/70 |
| 4,983,383 | 1/1991 | Maksimoski | 424/70 |
| 5,018,990 | 5/1991 | Martin et al. | 424/70 |
| 5,085,857 | 2/1992 | Reid et al. | 424/70 |

FOREIGN PATENT DOCUMENTS

| | | |
|---|---|---|
| 0 413 416 | 2/1991 | European Pat. Off. . |
| 0 413 417 | 2/1991 | European Pat. Off. . |
| 0 432 951 A2 | 6/1991 | European Pat. Off. . |
| 54-129135 | 10/1979 | Japan . |
| 56-72095 | 6/1981 | Japan . |
| 2262-506-A | 3/1989 | Japan . |
| 2262507-A | 3/1989 | Japan . |
| 327266 | 7/1989 | Japan . |
| 2042008 | 2/1990 | Japan . |
| 2188518 | 7/1990 | Japan . |
| 2188519 | 7/1990 | Japan . |
| 849433 | 9/1960 | United Kingdom . |

OTHER PUBLICATIONS

McCutcheons's *Emulsifiers & Detergents*, 1981 International Edition, pp. 55 and 157.

Caelles, J., Comelles, F., Leal, J.S., Para, J.L. and Anguera, S., "Anionic and Cationic Compounds in Mixed Systems", *Cosmetics & Toiletries*, vol. 106, Apr. 1991, pp. 49–54.

Burgess, D. J., "Practical Analysis of Complex Coacervate Systems, *J. Colloid and Interface Science*", vol. 140, No. 1, Nov. 1990, pp. 227–228.

vonOss, C.J., "Coacervation, Complex–Coacervation and Flocculation", *J. Dispersion Science and Technology*, vol. 9 (Nos. 5 and 6), 1988–1989, pp. 561–573 Amerchol Corp. pamphlet Glucam®.

McCutcheon's functional Materials 1990, McCutcheon Publishing Co., Glen Rock, NJ, pp. 48, 69.

Hardman and Jorkelson, General Electric Co., "Silicones", reprinted from Eneg. of Polymer Science & Engineering, vol. 15, 2nd Ed., 1989, J. Wiley & Sons, Inc., pp. 265–270.

*Primary Examiner*—Douglas J. McGinty
*Assistant Examiner*—Charles Boyer
*Attorney, Agent, or Firm*—Leonard W. Lewis; Loretta J. Henderson; David K. Dabbiere

[57] ABSTRACT

Disclosed are hair conditioning shampoo compositions comprising (a) from about 5% to about 50%, by weight, of an anionic surfactant component;

(b) from about 0.1% to about 10%, by weight, of a dispersed, insoluble, nonionic silicone hair conditioning agent, said silicone hair conditioning agent comprising a non-volatile, insoluble, nonionic silicone fluid component;

(c) from about 0.2% to about 10%, by weight, of a soluble cationic, amino or quaternary ammonium conditioning surfactant having a cationic nitrogen atom and at least one N-radical containing one or more hydrophilic moieties that are within 4 carbon atoms (inclusive) of a cationic nitrogen, said hydrophilic moieties being selected from the group consisting of alkoxy, polyoxyalkylene, alkylamido, hydroxyalkyl, and alkylester moieties, and combinations thereof; and (d) an aqueous carrier.

The shampoo compositions hereof can provide excellent overall hair conditioning benefits, in conjunction with excellent cleaning performance, to a variety of hair types including treated hair such as permed and color-treated hair, as well as undamaged hair.

32 Claims, No Drawings

SHAMPOO COMPOSITIONS WITH SILICONE AND CATIONIC SURFACTANT CONDITIONING AGENTS

This application is a continuation of Ser. No. 08/260,619 filed Jun. 16, 1994, now abandoned, which is a continuation of Ser. No. 08/074,700 Jun. 10, 1993, now abandoned, which is a continuation of Ser. No. 07/852,363 Mar. 13, 1992, now abandoned, which is a continuation of Ser. No. 07/622,705 filed Dec. 5, 1990, now abandoned.

FIELD OF THE INVENTION

This invention relates to shampoo compositions comprising anionic detersive surfactants, silicone hair conditioning agents, and cationic surfactant hair conditioning agents.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. Shampooing can also result in the hair becoming dry or "frizzy" due to removal of natural oils or other hair moisturizing materials. After shampooing, the hair can also suffer from a loss of "softness" perceived by the user upon drying. A variety of approaches have been developed to alleviate the after-shampoo problems. These range from the inclusion of hair conditioning aids in shampoos to post-shampoo application of hair conditioners, i.e., hair rinses. Hair rinses are generally liquid in nature and must be applied in a separate step following the shampooing, left on the hair for a length of time, and rinsed with fresh water. This, of course, is time consuming and is not convenient.

While a wide variety of shampoos have been disclosed which contain conditioning aids, they have not been totally satisfactory for a variety of reasons. One problem relates to compatibility problems between good cleaning anionic surfactants and the many conventional cationic agents which historically have been used as conditioning agents.

Whereas efforts have been made to minimize adverse interaction through the use of alternate surfactants and improved cationic conditioning agents, it remains highly desirable to utilize anionic surfactants in shampoo compositions. Furthermore, cationic conditioning agents commonly do not provide optimal overall conditioning benefits, particularly in the area of "softness", when delivered as an ingredient in a shampoo composition. For example, cationic surfactants which are compatible with the anionic detersive surfactants and which have previously been incorporated into shampoo compositions, such as tricetyl methyl ammonium chloride, can provide good anti-static benefits, but are less successful at providing soft, conditioned hair.

Materials which can provide increased softness are nonionic silicones. Silicones in shampoo compositions have been disclosed in a number of different publications. Such publications include U.S. Pat. No. 2,826,551, Geen, issued Mar. 11, 1958; U.S. Pat. No. 3,964,500, Drakoff, issued Jun. 22, 1976; U.S. Pat. No. 4,364,837, Pader, issued Dec. 21, 1982; and British Patent 849,433, Woolston, issued Sep. 28, 1960. While these patents disclose silicone containing compositions, they also did not provide a totally satisfactory product in that it was difficult to maintain the silicone well dispersed and suspended in the product. Recently, stable, insoluble silicone-containing hair conditioning shampoo compositions have been described in U.S. Pat. No. 4,741,855, Grote and Russell, issued May 3, 1988 and U.S. Pat. No. 4,788,006, Bolich and Williams, issued Nov. 29, 1988. These shampoo compositions can deliver excellent overall conditioning benefits to the hair while maintaining excellent cleaning performance, even with the use of anionic detersive surfactants, for a wide variety of hair types. However, it would be desirable to improve these types of shampoos such that they provided improved conditioning benefits to one type of hair in particular, that type being hair damaged by permanent treatments (i.e., "perms"), color treatments, and bleach treatments, applied either at hair salons or at home. Unfortunately, silicone hair conditioner efficacy for permed hair appears to be lower than that for most undamaged hair. It would be desirable to provide a shampoo composition that would provide excellent overall cleaning and conditioning benefits for such hair, as well as other types of hair not subjected to such treatments. This would reduce the need for families or others sharing hair care products to purchase separate shampoo and conditioning products for persons with damaged and undamaged hair.

It is an object of this invention to provide shampoo compositions, which can provide excellent cleaning performance and excellent overall hair conditioning for such damaged hair as well as for hair not subjected to such treatments ("undamaged hair").

It is a further object of this invention to provide improved anionic surfactant-containing shampoo compositions that can provide excellent cleaning performance and conditioning performance for both damaged and undamaged hair types, such that the shampooed hair can have desirable levels of manageability, combability, softness, and low or reduced levels of dryness.

These objects will become apparent from the description which follows, as many other objects become apparent upon a reading of said description.

Unless otherwise indicated, all percentages are calculated by weight of the total composition, and all ratios are calculated on a weight basis.

SUMMARY OF THE INVENTION

This invention provides anionic detersive surfactant-containing liquid shampoo compositions that can provide both excellent cleaning performance and hair conditioning benefits to a wide variety of hair types, including treatment damaged and undamaged hair. This can be attained by incorporating into the shampoo composition a nonionic, insoluble, nonvolatile silicone hair conditioning agent and, additionally, critically selected, soluble cationic conditioning surfactants. The shampoo compositions hereof will also comprise an aqueous carrier.

The cationic surfactants of the present invention are quaternary ammonium surfactants and amine surfactants that are positively charged at the pH of the shampoo composition, generally at pH of about 10 or lower and are soluble in the shampoo composition. The cationic surfactants for use herein must also contain one or more nonionic hydrophilic moieties. Without intending to necessarily limit the invention by any particular theory, it is believed that the presence of nonionic hydrophilic moieties enhances the ability of the cationic surfactant to remain soluble in the shampoo compositions, thus enhancing hair conditioning efficacy of the cationic surfactant.

When combined with the nonionic silicone conditioning agents in the shampoo compositions of this invention, these cationic surfactants can provide surprisingly good hair conditioning benefits for permed or other damaged hair characterized by increased anionic character, such as bleached hair and color treated hair. These types of hair that have been damaged and are characterized by increased anionic character shall hereinafter be collectively referred to as "damaged hair". Nonionic silicone conditioning agents suffer from reduced deposition, and therefore reduced efficacy, for these hair types. On the other hand, the use of the cationic surfactants as the sole type of hair conditioning agents to damaged hair when delivered from shampoo compositions may not provide sufficient overall conditioning benefits, especially in the area of softness. The combination of hair conditioning agents, however, results in shampoo compositions with high levels of conditioning for damaged hair, and retains excellent conditioning for undamaged hair and cleaning performance for all hair types. As used herein, undamaged refers to hair that is not damaged by perms or other hair treatments which increase the anionic character of the hair, and does not exclude, for example, oily hair, dry hair, etc., or hair damaged in some other respect, unless such other damage is specifically and expressly indicated. These results are especially important because merely increasing the level of silicone conditioning agent in a particular shampoo that is effective for treating undamaged hair to improve conditioning of damaged hair can result in too high a level of silicone deposition for undamaged hair. This can impart an undesirable greasy feel. On the other hand, the cationic surfactant, by itself, does not provide efficient conditioning of undamaged hair. The present invention provides anionic detersive surfactant-containing shampoo compositions that can provide excellent conditioning to both damaged and normal hair through the use of nonionic silicone and particularly selected hydrophile-containing cationic conditioning surfactants hereof.

The preferred cationic conditioning surfactants for use in the present invention are those which are useful for providing conditioning benefits, particularly hair conditioning benefits and which are quaternary ammonium or amino compounds having at least one N-radical containing one or more hydrophilic moieties selected from alkoxy, polyoxyalkylene, alkylamido, hydroxyalkyl, and alkylester moieties, and combinations thereof. The amino surfactants must be positively charged at the pH of the shampoo composition. Generally, the pH of shampoo compositions will be less than about 10, typically from about 3 to about 9. A pH of about 9 or less is especially preferred for shampoo compositions containing cationic conditioning surfactants that are dependent upon amino moieties for their cationic charge.

In a preferred embodiment, the present invention provices hair conditioning shampoo compositions comprising:

(a) from about 5% to about 50%, by weight, of an anionic detersive surfactant component;

(b) from about 0.1% to about 10%, by weight, of a dispersed, insoluble, nonionic silicone conditioning agent, said silicone hair conditioning agent comprising a non-volatile, insoluble, nonionic, silicone fluid component;

(c) from about 0.2% to about 10%, by weight, of a soluble cationic, amino or quaternary ammonium conditioning surfactant having a cationic nitrogen atom and at least one N-radical containing one or more hydrophilic moieties that are within 4 carbon atoms (inclusive) of a cationic nitrogen atom, said hydrophilic moieties being selected from the group consisting of alkoxy, polyoxyalkylene, alkylamido, hydroxyalkyl, and alkylester moieties, and mixtures thereof; and (d) an aqueous carrier.

As used herein, the terms "soluble" and "insoluble" used in reference to particular ingredients of the shampoo compositions refer to solubility or insolubility, respectively, of that ingredient in the shampoo composition.

All percentages are calculated by weight of the total composition unless otherwise specifically indicated.

The invention, including preferred embodiments thereof, is described in further detail in the Detailed Description of the Invention, which follows.

DETAILED DESCRIPTION OF THE INVENTION

The essential as well as a variety of preferred and optional components of the compositions of the present invention are described below.

Anionic Detersive Surfactant

The hair conditioning shampoo compositions of the present invention comprise an anionic detersive surfactant to provide cleaning performance to the composition.

The anionic detersive surfactant will generally be from about 5% to about 50%, preferably from about 8% to about 30%, more preferably from about 10% to about 25%, of the composition. The anionic detersive surfactant of the compositions hereof can be a single species of surfactant or a combination of different surfactants.

Synthetic anionic detersive detergents useful herein include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohols having from about 8 to about 24 carbon atoms. Preferably, R has from about 12 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic detersive surfactants are the water-soluble salts of the organic, sulfuric acid reaction products of the general formula:

wherein $R_1$ is chosen from the group consisting of a straight or branched chain, saturated aliphatic hydrocarbon radical having from about 8 to about 24, preferably about 12 to about 18, carbon atoms; and N is a cation. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of synthetic anionic detersive surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other synthetic anionic detersive surfactants of this variety are set forth in U.S. Pat. Nos. 2,486,921; 2,486,922; and 2,396,278.

Still other synthetic anionic detersive surfactants are in the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic detersive surfactants utilizable olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having about 12 to about 24 carbon atoms, preferably about 14 to about 16 carbon atoms. Preferably, they are straight chain olefins. Examples of suitable 1-olefins include 1-dodecene; 1-tetradecene; 1-hexadecene; 1-octadecene; 1-etcosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880, Pflaumer and Kessler, issued Jul. 25, 1967, incorporated herein by reference.

Another class of anionic detersive surfactants are the β-alkyloxy alkane sulfonates. These compounds have the following formula:

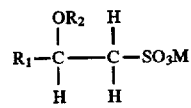

where $R_1$ is a straight chain alkyl group having from about 6 to about 20 carbon atoms, $R_2$ is a lower alkyl group having from about 1(preferred) to about 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein include: potassium-β-methoxydecanesulfonate, sodium 2-methoxy-tridecanesulfonate, potassium 2-ethoxytetradecylsulfonate, sodium 2-isopropoxyhexadecylsulfonate, lithium 2-t-butoxytetradecyl-sulfonate, sodium β-methoxyoctadecylsulfonate, and ammonium β-n-propoxydodecylsulfonate.

Many additional synthetic anionic surfactants are described in *McCutcheon's. Emulsifiers and Detergents*, 1989 Annual, published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference.

Preferred anionic detersive surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Optional Detersive Surfactants

In addition to the anionic detersive surfactant, the compositions of the present invention can optionally contain other detersive surfactants. These include nonionic surfactants, amphoteric surfactants, zwitterionic surfactants. Optional detersive surfactants, when used, are typically present at levels of from about 0.5% to about 20%, more typically from about 1% to about 10%. Also, the total amount of detersive surfactant in compositions containing optional detersive surfactants in addition to the anionic surfactant will generally be from about 5.5% to about 50%, preferably from about 8% to about 30%, more preferably from about 10% to about 25%. Cationic detersive surfactants can also be used, but are generally less preferred because they can adversely interact with the anionic detersive surfactant. Cationic detersive surfactants, if used, are preferably used at levels no greater than about 5%.

Nonionic detersive surfactants which can be used include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are 1. The polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oledimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl decyl methyl sulfoxide, 3-methoxytridecyl methyl sulfoxide, 3-hydroxytridecyl methyl sulfoxide, 3-hydroxy-4-dodecoxybutyl methyl sulfoxide.

Zwitterionic detersive surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2-Y(+)-CH_2-R^4-Z(-)$$
$$\overset{(R^3)_x}{|}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxy-propane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl) ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines can also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH(CH$_2$)$_3$ radical is attached to the nitrogen atom of the betaine are also useful in this invention. Preferred betaines for use in the present compositions are cocoamidopropyl betaine, cocobetaine, lauryl amidopropyl betaine, and oleyl betaine.

Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate cocoyl sarcosine, sodium 3-dodecylaminopropane sulfonate, sodium lauryl sarcosinate, sodium lauroyl sarcosinate, lauryl sarcosine N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378. An additional detersive surfactant suitable for use in the present invention is cocoamphocarboxy glycinate.

The most preferred shampoos of the present invention contain specific combinations of anionic surfactants, zwitterionic surfactants, and amphoteric surfactants. The preferred shampoos contain from about 2% to about 16% of alkyl sulfates, from 0% to about 14% of ethoxylated alkyl sulfates, and from about 0% to about 10% of an optional detersive surfactant selected from the nonionic, amphoteric, and zwitterionic detersive surfactants, with a total surfactant level of from about 10% to about 25%.

Silicon Hair Conditioning Agent

An essential component of the present invention is a nonionic silicone hair conditioning agent which is insoluble in the shampoo compositions hereof. The silicone conditioning agent comprises a silicone fluid component which contains a nonvolatile insoluble silicone fluid and optionally comprises a silicone gum which is insoluble in the shampoo composition as a whole but is soluble in the silicone fluid. The silicone hair conditioning agent can also comprise a silicone resin to enhance silicone fluid component deposition efficiency. The silicone hair conditioning agent may comprise volatile silicone components; however, such volatile silicones will preferably exceed no more than about 0.5%, by weight, of the shampoo composition.

The silicone hair conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Corning Corporate Test Method CTM0004, Jul. 20, 1970.

The shampoo compositions hereof will generally comprise from about 0.1% to about 10%, by weight, of the silicone hair conditioning agent, preferably from about 0.5% to about 8%, more preferably from about 1% to about 5%.

Suitable insoluble, nonvolatile silicone fluids include polyalkyl siloxanes, polyaryl siloxanes, polyalkylaryl siloxanes, polyether siloxane copolymer and mixtures thereof. However, other insoluble, nonvolatile silicone fluids having hair conditioning properties may be used. The term "nonvolatile" as used herein shall mean that the silicone material exhibits very low or no significant vapor pressure at ambient conditions, as is well understood in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000. The term "silicone", as used herein, shall be synonomous with the term "polysiloxane".

The nonvolatile polyalkylsiloxane fluids that may be used include, for example, polydimethyl siloxanes. These siloxanes are available, for example, from the General Electric Company as a Viscasil series and from Dow Corning as the Dow Corning 200 series.

The polyalkylaryl siloxane fluids that may be used, also include, for example, polmethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified dimethylpolysiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Silicone fluids hereof also include polyalkyl or polyaryl siloxanes with the following structure:

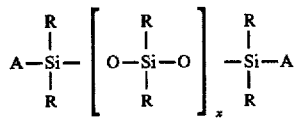

wherein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is *Silicon Compounds* distributed by Petrarch Systems, Inc., 1984. This reference provides an extensive (though not exclusive) listing of suitable silicone fluids.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, *Chemistry and Technology of Silicone*, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenylsiloxane) (methylvinylsiloxane) copolymer and mixtures thereof, Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30, preferably from about 40:60 to about 60:40.

Another optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, monomer units during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in an unhardened form in a low viscosity volatile or nonvolatile silicone fluid. The silicone resins for use herein should be supplied and incorporated into the present compositions in such unhardened form, as will be readily apparent to those skilled in the art.

Background material on silicones including sections discussing silicone fluids, gums, and resins, as well as manufacture of silicones, can be found in *Encyclopedia of Polymer Science and Engineering*, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetrafunctional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid component to the silicone resin component is from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above.

Cationic Conditioning Surfactant

The shampoo compositions of the present invention comprise one or more organic, soluble, cationic surfactants useful for the conditioning of hair, hereinafter "cationic conditioning agent", selected from the group consisting of quaternary ammonium surfactants and amino surfactants that are positively charged at the pH of the shampoo composition. The shampoo compositions will generally contain from about 0.2% to about 10%, preferably from about 0.5% to about 8%, more preferably from about 1% to about 5%, of the soluble cationic conditioning agent. As Just discussed, the cationic conditioning surfactant must be soluble in the shampoo composition, i.e., an amount of the cationic conditioning agent within the ranges set forth above should be solubilized in the shampoo composition. The cationic surfactants for use herein also must contain one or more nonionic hydrophilic moieties. Sufficient hydrophilic moieties must be present to maintain solubility subsequent to any ionic complexation that may occur between the cationic conditioning surfactants and the anionic detersive surfactants.

The preferred cationic conditioning surfactants for use in the present invention are those which are useful for providing conditioning benefits, particularly hair conditioning properties and which are quaternary ammonium or amino compounds having at least one N-radical containing one or more nonionic hydrophilic moieties selected from alkoxy, polyoxyalkylene, alkylamido, hydroxyalkyl, and alkylester moieties, and combinations thereof. The surfactant contains at least one hydrophilic moiety within 4 (inclusive), preferably within 3 (inclusive), carbon atoms of the quaternary nitrogen or cationic amino nitrogen. For purposes herein, this means that the closest non-carbon atom in the hydrophilic moiety to the cationic nitrogen must be within the stated number of carbon atoms relative to said nitrogen. Additionally, carbon atoms that are part of a hydrophilic moiety, e.g., carbon atoms in a hydrophilic polyoxyalkylene (e.g., —CH$_2$—CH$_2$—O—), that are adjacent to other hydrophilic moieties are not counted as when determining the number of hydrophilic moieties within 4, or preferably 3, carbon atoms of the cationic nitrogen. In general, the alkyl portion of any hydrophilic moiety is preferably a C$_1$-C$_3$ alkyl. Suitable hydrophile-containing radicals include, for example, ethoxy, propoxy, polyoxyethylene, polyoxypropylene, ethylamido, propylamido, hydroxymethyl, hydroxyethyl, hydroxypropyl, methylester, ethylester, propylester, or mixtures thereof, as nonionic hydrophile moieties. The amino surfactants must be positively charged at the pH of the shampoo compositions. Generally, the pH of the shampoo compositions will be less than about 10, typically from about 3 to about 9, preferably from about 4 to about 8. Additionally, it is preferred that the charge density be within the above limits at the pH of intended use which will, in general, be from about pH 4 to about pH 9, most preferably from about pH 5 to about pH 8. The polymer, of course, must remain cationic upon application to the hair in order for there to be adequate substantivity between the conditioning agent and the hair.

Among the quaternary ammonium cationic surfactants useful herein are those of the general formula:

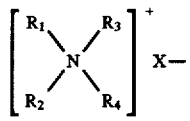
(I)

wherein R$_1$, R$_2$, R$_3$ and R$_4$ radicals comprise, independently, substituted or unsubstituted hydrocarbyl chains of from 1 to about 30 carbon atoms, or a hydrocarbyl having from 1 to about 30 carbon atoms and containing one or more aromatic, ether, ester, amido, or amino moieties present as substituents or as linkages in the radical chain, wherein at least one of the R$_1$-R$_4$ radicals contains one or more hydrophilic moieties selected from alkoxy (preferably C$_1$-C$_3$ alkoxy), polyoxyalkylene (preferably C$_1$-C$_3$ polyoxyalkylene), alkylamido, hydroxyalkyl, alkylester, and combinations thereof. Preferably, the cationic conditioning surfactant contains from 2 to about 10 nonionic hydrophile moieties located within the above stated ranges. For purposes herein, each hydrophilic amido, alkoxy, hydroxyalkyl, alkylester, alkylamido or other unit is considered to be a distinct nonionic hydrophile moiety. X is a soluble salt forming anion preferably selected from halogen (especially chlorine), acetate, phosphate, nitrate, sulfonate, and alkyl sulfate radicals.

Preferred quaternary ammonium salt surfactants include those of the formula

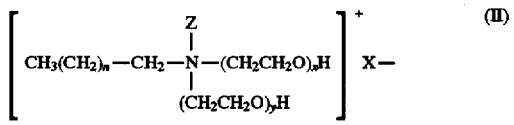
(II)

wherein n is from 8-28, preferably 16, x+y=2 to about 15. Z is a short chain alkyl, preferably a C$_1$-C$_3$ alkyl, more preferably methyl, and X is a water soluble salt forming anion (e.g., Cl, sulfate, etc.)

Other preferred quaternary ammonium salt surfactants include those of the formula

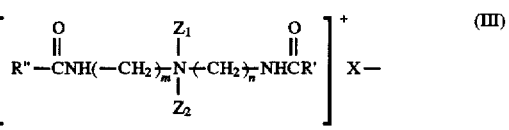
(III)

wherein Z$_1$ and Z$_2$ are, independently, substituted or unsubstituted hydrocarbyls, and, preferably, Z$_1$ is an alkyl, preferably a C$_1$-C$_3$ alkyl, more preferably methyl, and Z$_2$ is a short chain hydroxyalkyl, preferably hydroxymethyl or hydroxyethyl, n and m independently are integers from 2 to 4, inclusive, preferably from 2 to 3, inclusive, more preferably 2, R' and R", independently, are substituted or unsubstituted hydrocarbyls, preferably C$_{12}$-C$_{20}$ alkyl or alkenyl, and X is a soluble salt-forming anion (e.g., sulfate, Cl, etc.).

Still other quaternary ammonium salt surfactants are of the formulas:

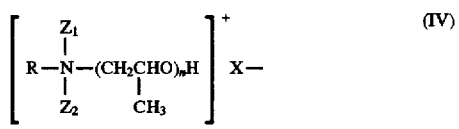
(IV)

wherein R is a hydrocarbyl, preferably a C$_1$-C$_3$ alkyl, more preferably ethyl, Z$_1$ and Z$_2$ are, independently, short chain hydrocarbyls, preferably C$_2$-C$_4$ alkyl or alkenyl, more preferably ethyl, n is from about 2 to about 40, preferably from about 7 to about 30, and X is a soluble salt-forming onion, as set forth previously;

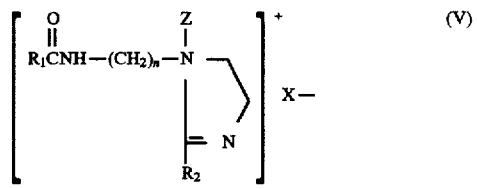
(V)

wherein R$_1$ and R$_2$ , independently, are C$_{12}$-C$_{20}$ hydrocarbyls, preferably C$_{16}$-C$_{18}$ alkyl or alkenyls (e.g., those derived from tallow acid), Z is a C$_1$-C$_3$ hydrocarbyl, preferably ethyl, n is 2 or 3, and X is a soluble salt forming anion; and

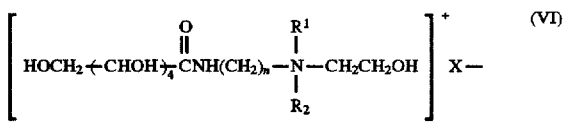
(VI)

wherein n is 2 or 3, R$_1$ and R$_2$, independently are C$_1$-C$_3$ hydrocarbyls preferably ethyl, and X is as defined above.

Specific examples of preferred quaternary ammonium salts include polyoxyethylene (2) stearyl ethyl ammonium chloride, methyl bis (hydrogenated tallowamidoethyl) 2-hydroxyethyl ammonium methyl sulfate, polyoxypropylene (9) diethyl methyl ammonium chloride, tripolyoxyethylene (total PEG=10) stearyl ammonium phosphate, bis(N-hydroxyethyl-2-oleyl imidazolinium chloride) polyethylene glycol (12), and isododecylbenzyl triethanolammonium chloride.

Other ammonium quaternary and amino surfactants include those of the above general formula 1 in the form of ring structures formed by covalently linking of the radicals. Examples of such cationic surfactants include imidazolines, imidazoliniums, and pyridiniums, etc., wherein said surfactant has at least one nonionic hydrophile-containing radical as set forth above. Specific examples include 2-heptadecyl-4,5-dihydro-1H-imidazol-1-ethanol, 4,5-dihydro-1-(2-hydroxyethyl)-2-isoheptadecyl-1-phenylmethylimidazolium chloride, and 1-[2-oxo-2-[[2-[(1-oxooctadecyl)oxy]ethyl]amino]ethyl] pyridinium chloride. See also, for example formula V Salts of primary, secondary and tertiary fatty amines are also preferred cationic surfactant materials. The alkyl groups of such amines preferably have from about 1 to about 30 carbon atoms and must contain at least one, preferably 2 to about 10, nonionic hydrophilic moieties selected from alkoxy, polyoxyalkylene, alkylamido, hydroxyalkyl, and alkylester moieties, and mixtures thereof. Secondary and tertiary amines are preferred, tertiary amines are particularly preferred. Specific examples of suitable amines include diethyl aminoethyl polyoxyethylene (5) laurate, coco-polyglyceryl-4 hydroxypropyl dihydroxy ethylamine, and dihydroxyethyl tallowamine hydrochloride.

The cationic conditioning agents for use herein may also include a plurality of ammonium quaternary moieties or amino moieties, or a mixture thereof.

Aqueous Carrier

The shampoo compositions of the present invention are liquids which, preferably, and are pourable at room temperature. The compositions hereof will comprise an aqueous carrier, i.e., water, which will generally be present at a level of about 20% to about 95% by weight of the composition, preferably from about 60% to about 85% for pourable, liquid formulations. The compositions of the present invention can also be in other forms, such as gels, mousses, etc. In such cases, appropriate components known in the art such as gelling agents (e.g., hydroxyethyl cellulose), etc. can be included in the compositions. Gels will typically contain from about 20% to about 90% water. Mousses will contain aerosol propellant in a low viscosity composition and are packaged in an aerosol can, according to techniques well know in the art.

Suspending Agent for Silicone Conditioning Agent

Since the silicone conditioning agent used in the present compositions is an insoluble silicone dispersed in the compositions, it is preferred to utilize a suspending agent for the silicone. Suitable suspending agents are long chain acyl derivatives, long chain amine oxides, and mixtures thereof, wherein such suspending agents are present in the shampoo compositions in crystalline form. A variety of such suspending agents are described in U.S. Pat. No. 4,741,855, Grote et al., issued May 3, 1988. Especially preferred is ethylene glycol distearate.

Also included among the long chain acyl derivatives useful as suspending agents are the N,N-di(hydrogenated) $C_{16}$–$C_{18}$ amido benzoic acid, or soluble salt (e.g., K, Na salts) thereof particularly N,N-di(hydrogenated)tallow amido benzoic acid which is commercially marketed by Stepan Company (Northfield, Ill., USA).

Another useful suspending agent for the silicone conditioning agents of the present compositions is xanthan gum as described in U.S. Pat. No. 4,788,006, Bolich et al., issued Nov. 29, 1988. The combination of long chain acyl derivatives and xanthan gum as a suspending system for silicone is described in U.S. Pat. No. 4,704,272, Oh et al., issued Nov. 3, 1987, and may also be used in the present compositions.

Generally, the shampoo compositions will comprise from about 0.1% to about 5.0%, preferably from about 0.5% to about 3.0%, of the suspending agent to suspend the silicone conditioning agent.

Optional Components

The present compositions may also comprise a variety of non-essential, optional shampoo components suitable for rendering such compositions more cosmetically or aesthetically acceptable or to provide them with additional usage benefits. A variety of such ingredients are well-known to those skilled in the art, and these include without limiting the invention thereto: pearlescent aids, such as $TiO_2$ coated mica, ethylene glycol distearate; opacifiers; preservatives, such as benzyl alcohol, 1,3-bis(hydroxymethyl)-5,5 dimethyl-2,4-imidazolidinedione (e.g. Glydant®, Glyco, Inc., Greenwich, Conn., USA), methylchloroisothiazolinone (e.g. Kathon®, Rohm & Haas Co., Philadelphia, Pa., USA), methyl paraben, propyl paraben, and imidazolidinyl urea; fatty alcohols, such as cetearyl alcohol, cetyl alcohol, and stearyl alcohol; sodium chloride; sodium sulfate; ethyl alcohol; pH adjusting aids, such as citric acid, sodium citrate, succinic acid, phosphoric acid, monosodium phosphate, disodium phosphate, sodium hydroxide, and sodium carbonate; coloring agents or dyes; perfumes; and sequestering agents, such as disodium ethylenediamine tetra-acetate.

Another optional ingredient that can be advantageously used is an anti-static agent. The anti-static agent should not unduly interfere with the in-use performance and end-benefits of the shampoo; particularly, the anti-static agent should not interfere with (i.e., it should be compatible with) the anionic detersive surfactant. An especially suitable anti-static agent is tricetyl methyl ammonium salt (e.g., the chloride salt, "TCMAC").

Preferred compositions herein comprise anionic surfactant, silicone conditioning agent, TCMAC (or other salt thereof), and soluble cationic conditioning surfactant selected from the compounds of Formula III, above, especially the preferred embodiments of Formula III. Surprisingly, such compositions can exhibit enhanced silicone conditioning agent deposition relative to similar compositions absent the soluble cationic conditioning surfactant.

Typically, from about 0.1% to about 5% of such anti-static agent is incorporated into the shampoo compositions when they are to be utilized.

Though the silicone suspending agent component may act to thicken the present compositions to some degree, the present compositions may also optionally contain other thickeners and viscosity modifiers such as an ethanolamide of a long chain fatty acid (e.g., polyethylene (3) glycol lauramide and coconut monoethanolamide).

These optional components generally are used individually in the compositions of the present invention at a level of from about 0.01% to about 10%, preferably from about 0.05% to about 5.0% of the shampoo composition.

The pH of the present compositions will generally be in the range of from about 2 to about 10, preferably from about 3 to about 9.

Method of Manufacture

The compositions of the present invention, in general, can be made by mixing the materials together at elevated temperature, e.g., about 72° C. The silicone resin, if any, and silicone fluid component are first mixed together before being mixed with the other ingredients. The complete mixture is mixed thoroughly at the elevated temperature and is then pumped through a high shear mill and then through a heat exchanger to cool it to ambient temperature. The average particle size of the silicone is preferably from about 0.5 microns to about 20 microns. Alternately, the silicone conditioning agent can be mixed with anionic surfactant and fatty alcohol, such as cetyl and stearyl alcohols, at elevated temperature, to form a premix containing dispersed silicone.

The premix can then be added to and mixed with the remaining materials of the shampoo, pumped through a high shear mill, and cooled.

Method of Use

The shampoo compositions of the present invention are utilized conventionally, i.e., the hair is shampooed by applying an effective amount of the shampoo composition to the scalp, and then rinsing it out. Application of the shampoo to the scalp in general, encompasses massaging or working the shampoo in the hair such that all or most of the hair on the scalp is contacted. The term an "effective amount" as used herein, is an amount which is effective in cleaning and conditioning the hair. Generally, from about 1 g to about 20 g of the composition is applied for cleaning and conditioning the hair.

EXAMPLES

The following examples illustrate the present invention. It will be appreciated that other modifications of the present invention within the skill of those in the hair care formulation art can be undertaken without departing from the spirit and scope of this invention.

All parts, percentages, and ratios herein are by weight unless otherwise specified. Some components may come from suppliers as solutions. The levels given reflect the active weight percent of such materials, unless otherwise specifically indicated.

Example I

The following is a shampoo composition of the present invention.

| Component | Weight % |
| --- | --- |
| Ammonium Lauryl Sulfate | 13.5 |
| Ammonium Laureth (3) Sulfate | 4.0 |
| Methyl bis(hydrogenated tallow amidoethyl) 2-hydroxyethyl ammonium methyl sulfate * | 1.5 |
| Coconut Monoethanol Amide | 1.0 |
| Ethylene Glycol Distearate | 1.5 |
| Ammonium Xylene Sulfonate | 1.0 |
| Xanthan Gum | 0.5 |
| Polydimethylsiloxane ** | 3.0 |
| Cetyl Alcohol | 0.4 |
| Stearyl Alcohol | 0.2 |
| Perfume | 1.2 |
| Color Solution | 0.6 |
| Preservative | 0.2 |
| Water and Minor | -- to 100% -- |

* Available under the tradename VARISOFT 110 from Sherex Chemical Co. (Dublin, Ohio, USA)
** A 40/60 weight ratio blend of polydimethylsiloxane gum (GE SE76, General Electric Co., Silicone Products Div., Waterford, NY, USA) and a polydimethylsiloxane fluid (about 350 centistokes).

The composition can provide excellent in-use hair cleaning and conditioning, for both damaged and undamaged, hair types.

Example II

The following is an example of a shampoo composition of the present invention.

| Component | Weight % |
| --- | --- |
| Ammonium Lauryl Sulfate | 13.0 |
| Ammonium Laureth (3) Sulfate | 5.0 |
| Polyoxyethylene (2) stearyl methyl ammonium chloride * | 1.0 |
| Coconut Monoethanol Amide | 1.5 |
| Ethylene Glycol Distearate | 2.0 |
| Ammonium Xylene Sulfonate | 1.0 |
| Polydimethylsiloxane ** | 2.5 |
| Cetyl Alcohol | 0.4 |
| Stearyl Alcohol | 0.2 |
| Perfume | 1.2 |
| Color Solution | 0.6 |
| Preservative | 0.2 |
| Water and Minors | -- to 100% -- |

* Available under the tradename ETHOQUAD 18/12 from Armak Company (McCook, Illinois, USA).
** A 40/60 weight ratio blend of polydimethylsiloxane gum (GE SE76, General Eleactric Co., Silicone Products Div., Waterford, NY, USA) and a polydimethylsiloxane fluid (about 350 centistokes).

The composition can provide excellent in-use hair cleaning and conditioning, for both damaged and undamaged, hair types.

Example III

The following is an example of a shampoo composition of the present invention.

| Component | Weight % |
| --- | --- |
| Ammonium Lauryl Sulfate | 13.5 |
| Ammonium Laureth (3) Sulfate | 4.0 |
| Polyoxyethylene (2) stearyl methyl ammonium chloride * | 1.5 |
| Coconut Monoethanol Amide | 1.5 |
| Ethylene Glycol Distearate | 2.0 |
| Trimethylsiloxysilicate | 0.1 |
| Polydimethylsiloxane ** | 2.0 |
| Cetyl Alcohol | 0.4 |
| Stearyl Alcohol | 0.2 |
| Perfume | 1.2 |
| Color Solution | 0.6 |
| Preservative | 0.2 |
| Water and Minors | -- to 100% -- |

* Available under the tradename ETHOQUAD 18/12 from Armak Company (McCook, Illinois, USA).
** A 40/60 weight ratio blend of polydimethylsiloxane gum (GE SE76, General Eleactric Co., Silicone Products Div., Waterford, NY, USA) and a polydimethylsiloxane fluid (about 350 centistokes).

The composition can provide excellent in-use hair cleaning and conditioning, for both damaged and undamaged, hair types.

Example IV

The following is an example of a shampoo composition of the present invention.

| Component | Weight % |
| --- | --- |
| Ammonium Lauryl Sulfate | 4.0 |
| Cocoamidopropyl Betaine | 3.5 |
| Ammonium Laureth (3) Sulfate | 9.0 |
| Sodium N-Lauryl β-Iminodipropionate | 4.0 |
| Methyl bis (hydrogenated tallow amidoethyl) 2-hydroxyethyl ammonium methyl sulfate * | 1.0 |
| Coconut Monoethanol Amide | 2.0 |
| Ethylene Glycol Distearate | 2.0 |
| Xanthan Gum | 0.5 |
| Polydimethylsiloxane ** | 2.0 |
| Cetyl Alcohol | 0.4 |

-continued

| Component | Weight % |
| --- | --- |
| Stearyl Alcohol | 0.2 |
| Perfume | 1.2 |
| Color Solution | 0.6 |
| Preservative | 0.2 |
| Water and Minors | -- to 100% -- |

\* Available under the tradename VARISOFT 110 from Sherex Chemical Co. (Dublin, Ohio, USA)
\*\* A 40/60 weight ratio blend of polydimethylsiloxane gum (GE SE76, General Electric Co., Silicone Products Div., Waterford, NY, USA) and a polydimethylsiloxane fluid (about 350 centistokes).

The composition can provide excellent in-use hair cleaning and conditioning, for both damaged and undamaged, hair types.

Example V

The following is a shampoo composition of the present invention.

| Component | Weight % |
| --- | --- |
| Ammonium Lauryl Sulfate | 8.5 |
| Ammonium Laureth (3) Sulfate | 8.5 |
| Methyl bis(hydrogenated tallow amidoethyl) 2-hydroxyethyl ammonium methyl sulfate \* | 2.0 |
| Coconut Monoethanol Amide | 1.5 |
| Ethylene Glycol Distearate | 2.0 |
| Ammonium Xylene Sulfonate | 1.5 |
| Tricetyl Methyl Ammonium Chloride | .5 |
| Polydimethylsiloxane Fluid \*\* | 1.4 |
| MQ Silicone Resin/Volatile Cyclomethicone \*\*\* | .1 |
| Cetyl Alcohol | .4 |
| Stearyl Alcohol | .2 |
| Perfume | 1.0 |
| Color Solution | .6 |
| Preservative | .03 |
| Water and Minors | -- to 100% -- |

\* Available under the tradename VARISOFT 110 from Sherex Chemical Co. (Dublin, Ohio, USA)
\*\* A 40/60 weight ratio blend of polydimethylsiloxane gum (GE SE76, General Electric Co., Silicone Products Div., Waterford, NY, USA) and a polydimethylsiloxane fluid (about 350 centistokes).
\*\*\* A 60:40 weight ratio blend of the MQ resin in volatile silicone carrier. M:Q molar ratio of about 0.8:1.0.

The composition can provide excellent in-use hair cleaning and conditioning, for both damaged and undamaged, hair types.

The compositions hereof can be made by preparing a premix of the entire amount of silicone conditioning agent (i.e., the silicone fluid component and, if any, the silicone resin) to be incorporated into the shampoo, along with sufficient ammonium laureth sulfate and cetyl and stearyl alcohol such that the premix comprises about 30% silicone conditioning agent, about 69% surfactant, and about 1% of the alcohols. The premix ingredients are heated and stirred at 72° C. for about 10 minutes and the premix is then conventionally mixed with the remaining hot ingredients. The composition is then pumped through a high shear mixer and cooled.

What is claimed is:

1. A liquid hair conditioning shampoo composition comprising:
   (a) from about 5% to about 50%, by weight, of an anionic surfactant component selected from the group consisting of:
      (i) alkyl sulfates;
      (ii) ethoxylated alkyl sulfates;
      (iii) succinamates;
      (iv) olefin sulfates having about 12 to about 24 carbons;
      (v) β-alkyloxy alkane sulfonates;
      (vi) reaction products of fatty acids esterified with isethionic acid and neutralized with sodium hydroxide;
      (vii) $R_1$—$SO_3$—M water-soluble salts wherein $R_1$ is a saturated aliphatic hydrocarbon radical having from about 8 to about 24, carbon atoms and M is a cation; and
      (viii) mixtures thereof;
   (b) from about 0.1% to about 10%, by weight, of a dispersed, insoluble, nonionic silicone hair conditioning agent comprising a non-volatile, insoluble, non-ionic silicone fluid component and a silicone resin component supplied in a nonvolatile silicone fluid, wherein the weight ratio of the nonvolatile silicone fluid component to the silicone resin component is from about 19:1 to about 400:1;
   (c) from about 0.2% to about 10%, by weight, of a soluble cationic, amino or quaternary ammonium conditioning surfactant having a cationic nitrogen atom and at least one N-radical containing one or more hydrophilic moieties that are within 4 carbon atoms, inclusive, of a cationic nitrogen, said hydrophilic moieties being selected from the group consisting of alkoxy, polyoxyalkylene, alkylamido, hydroxyalkyl, and alkylester moieties, and combinations thereof; wherein said soluble, cationic conditioning surfactant is selected from the group consisting of:

(i) 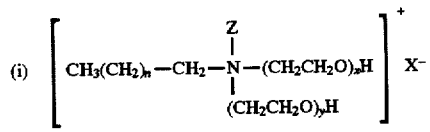

wherein n is from 8–28, x+y=2 to about 15, Z is a $C_1$–$C_3$ alkyl, and X is a water soluble salt forming anion;

(ii) 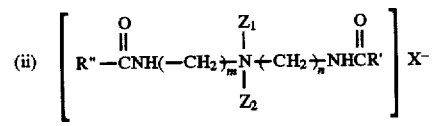

wherein $Z_2$ is a $C_1$–$C_3$ alkyl, $Z_2$ is a $C_1$–$C_3$ hydroxy alkyl, n and m independently are integers from 2 to 4, inclusive, R' and R" independently are substituted or unsubstituted hydrocarbyls, and X is a soluble salt-forming anion;

(iii) 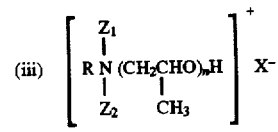

wherein R is a $C_1$–$C_3$ alkyl, $Z_1$ and $Z_2$ are independently, $C_2$–$C_4$ alkyl or alkenyl, n is from about 2 to about 40, and X is a soluble-salt forming anion;

(iv) 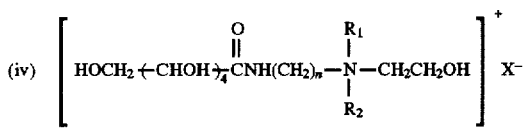

wherein n is 2 or 3, $R_1$ and $R_2$ independently are $C_1$–$C_3$ hydrocarbyls and X is a soluble salt-forming anion;

(v) 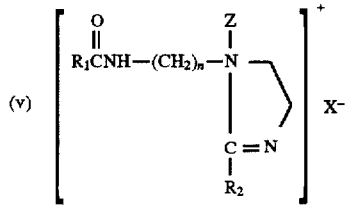

wherein $R_1$ and $R_2$, independently, are $C_{12}$–$C_{20}$ hydrocarbyls, Z is a $C_1$–$C_3$ hydrocarbyl, n is 2 or 3, and X is a soluble salt forming anion;

(vi) salts of primary, secondary and tertiary fatty amines: and (vii) mixtures thereof;

(d) from about 0.1% to about 20% of a detersive surfactant selected from the group consisting of nonionic, zwitterionic and amphoteric surfactants, and mixtures thereof; and (e) an aqueous carrier; wherein the composition is essentially free from volatile silicone.

2. A liquid hair conditioning shampoo composition as in claim 1, further comprising a suspending agent for said silicone hair conditioning agent.

3. A liquid hair conditioning shampoo composition, as in claim 2, wherein said shampoo composition comprises from about 0.5% to about 8% of said cationic surfactant, said cationic conditioning surfactant containing from 2 to about 10 of said hydrophilic moieties within 3 carbon atoms inclusive of a cationic nitrogen.

4. A liquid hair conditioning shampoo according to claim 3 wherein said soluble, cationic conditioning surfactant is selected from the group consisting of polyoxyethylene (2) stearyl methyl ammonium chloride, methyl bis (hydrogenated tallowamidoethyl) 2-hydroxyethyl ammonium methyl sulfate, bis(N hydroxyethyl-2-oleyl imidazolinium chloride) polyethylene glycol (12), isododecylbenzyl triethanolammonium chloride, 2-heptadecyl-4,5 dihydro-1H-imidazol-1-ethanol, 4,5-dihydro-1-(2-hydroxyethyl)-2-isohepta-decyl-1 -phenylmethylimidazoliumchloride, 1-(2-oxo-2-((2-{(1-oxooctadecyl)oxy}ethyl) amino) ethyl) amino) ethyl) pyridium chloride, diethyl aminoethyl polyoxyethylene (5) laurate, coco-polyglyceryl-4hydroxypropyl dihydroxy ethylamine, dihydroxyethy tallowamine hydrochloride, and mixtures thereof.

5. A liquid hair conditioning agent as in claim 1, wherein said soluble, cationic conditioning agent is selected from the group consisting of:

(i) 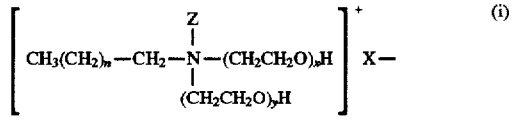

wherein n is from 8–28, x+y=2 to about 15, Z is a $C_1$–$C_3$ alkyl, and X is a water soluble salt forming anion;

(ii) 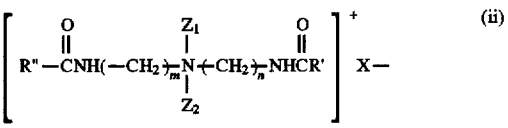

wherein $Z_1$ is a $C_1$–$C_3$ alkyl, $Z_2$ is a $C_1$–$C_3$, hydroxyalkyl, n and m independently are integers from 2 to 4, inclusive, R' and R", independently, are substituted or unsubstituted hydrocarbyls, and X is a soluble salt-forming anion;

(iii) 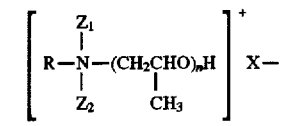

wherein R is a $C_1$–$C_3$ alkyl, $Z_1$ and $Z_2$ are, independently, $C_2$–$C_4$ alkyl or alkenyl, n is from about 7 to about 30, and X is a soluble-salt forming anion; and (iv) 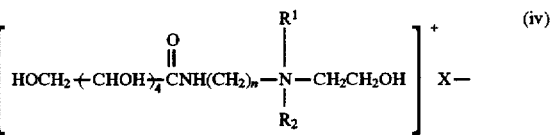

wherein n is 2 or 3, $R_1$ and $R_2$ independently are $C_1$–$C_3$ hydrocarbyls and X is a soluble salt-forming anion; and mixtures thereof.

6. A shampoo composition as in claim 2, wherein said anionic detersive surfactant component is selected from the group consisting of alkyl sulfates, ethoxylated alkyl sulfates, and mixtures thereof.

7. A shampoo composition as in claim 4, wherein said anionic detersive surfactant component is selected from the group consisting of alkyl sulfates, ethoxylated alkyl sulfates, and mixtures thereof.

8. A shampoo composition as in claim 7 wherein the anionic surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, aluric monoglyceride sodium sulfate, sodium lauryl sulfate, sodium laureth sulfate, potassium lauryl sulfate, potassium laureth sulfate, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, sodium tridecyl benzene sulfonate, sodium dodecyl benzene sulfonate, and mixtures thereof.

9. A shampoo composition as in claim 7, comprising from about 1% to about 10% of a detersive surfactant selected from the group consisting of nonionic, zwitterionic, and amphoteric surfactants, and mixtures thereof; and from about 10% to about 25% of the anionic surfactant; and wherein the total amount of detersive surfactant is from about 8% to about 30%.

10. A shampoo composition as in claim 9 wherein the detersive surfactant is selected from the group consisting of betaines, amino propyl betaines, sarcosinates, cocoamphocarboxy glycinate, and mixtures thereof.

11. A shampoo composition as in claim 4 wherein the silicone conditioning agent is present at a level of from about 0.5% to about 8%.

12. A shampoo composition as in claim 1 wherein the silicone conditioning agent is present at a level of from about 0.5% to about 5% and comprises a silicone fluid component containing polydimethylsiloxane gum having a viscosity greater than about 1,000,000 centistokes, and a polydimethylsiloxane fluid having a viscosity of from about 10 centistokes to about 100,000 centistokes, wherein the ratio of gum to fluid is from about 30:70 to about 70:30.

13. A shampoo composition as in claim 2 in the form of a pourable liquid.

14. A method for improving deposition of nonionic silicone conditioning agent on hair comprising applying an effective amount of the composition of claim 1 to the hair and then rinsing said composition from the hair.

15. A method for cleaning and conditioning the hair comprising applying an effective amount of the composition of claim 2 to the hair and then rinsing said composition from the hair.

16. A liquid hair conditioning shampoo composition comprising:

(a) from about 5% to about 50%, by weight, of an anionic surfactant component selected from the group consisting of:
(i) alkyl sulfates;
(ii) ethoxylated alkyl sulfates;
(iii) succinamates:
(iv) olefin sulfates having about 12 to about 24 carbons;
(v) β-alkyloxy alkane sulfonates:
(vi) reaction products of fatty acids esterified with isethionic acid neutralized with sodium hydroxide;
(vii) $R_1$—$SO_3$—M water-soluble salts wherein $R_1$ is a saturated aliphatic hydrocarbon radical having from about 8 to about 24 carbon atoms and M is a cation; and
(viii) mixtures thereof;

(b) from about 0.1% to about 10%, by weight, of a dispersed, insoluble, nonionic silicone hair conditioning agent comprising a non-volatile, insoluble, nonionic silicone fluid component and a silicone resin component supplied in a nonvolatile silicone fluid, wherein the weight ratio of the nonvolatile silicone fluid component to the silicone resin component is from about 19:1 to about 400:1;

(c) from about 0.2% to about 10%, by weight, of a soluble cationic conditioning surfactant selected from the group consisting of:

(i) 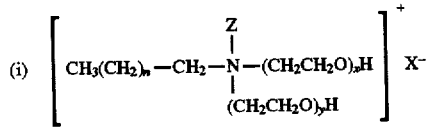

wherein n is from 8–28, x+y=2 to about 15 Z is a $C_1$–$C_3$ alkyl, and X is a water soluble salt forming anion;

(ii) 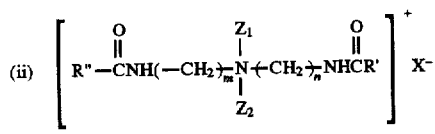

wherein $Z_1$ is a $C_1$–$C_3$ alkyl, $Z_2$ is a $C_1$–$C_3$ hydroxy alkyl, n and m independently are integers from 2 to 4 inclusive R' and R" independently are substituted or unsubstituted hydrocarbyls and X is a soluble salt-forming anion;

(iii) 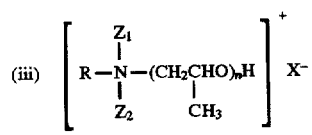

wherein R is a $C_1$–$C_3$ alkyl, $Z_1$ and $Z_2$ are, independently, $C_2$–$C_4$ alkyl or alkenyl, n is from about 2 to about 40, and X is a soluble-salt forming anion;

(iv) 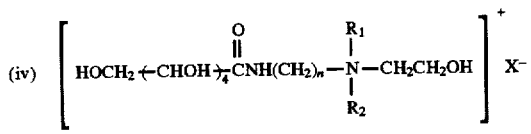

wherein n is 2 or 3, $R_1$ and $R_2$ independently are $C_1$–$C_3$ hydrocarbyls and X is a soluble salt-forming anion;

(v) 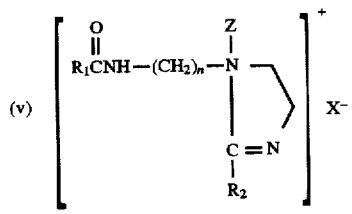

wherein $R_1$ and $R_2$ independently are $C_{12}$–$C_{20}$ hydrocarbyls, Z is a $C_1$–$C_3$ hydrocarbyl, n is 2 or 3, and X is a soluble salt forming anion;
(vi) salts of primary, secondary and tertiary fatty amines; and
(vii) mixtures thereof;

(d) an aqueous carrier; and (e) from about 0.1% to about 5% of an additional cationic component, said additional cationic component being an anionic surfactant compatible, cationic anti-static agent, wherein the composition is essentially free of volatile silicone.

17. A liquid hair conditioning shampoo composition as in claim 16, wherein the additional cationic component is tricetyl methyl ammonium salt and the alkyl portion of at least one soluble cationic conditioning surfactant hydrophilic moiety is a $C_1$–$C_3$ alkyl group.

18. A liquid hair conditioning shampoo composition as in claim 16, wherein (a) the soluble cationic conditioning surfactant hydrophilic moieties are selected from the group consisting of alkoxy, alkyl amino, hydroxyalkyl and alkylester moieties, combinations thereof, combinations of at least one of said moieties and at least one polyoxyalkylene, or (b) the soluble cationic conditioning surfactant is of the formula:

(i) 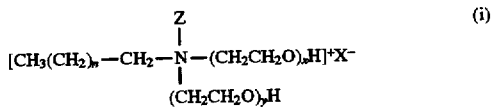

wherein n is from 8–28, x+y=2 to about 15, Z is a $C_1$–$C_3$ alkyl and X is a water soluble salt forming anion.

19. A liquid hair conditioning shampoo composition comprising:
(a) from about 5% to about 50% by weight, of an anionic surfactant component selected from the group consisting of:

(i) alkyl sulfates;
(ii) ethoxylated alkyl sulfates;
(iii) succinamates;
(iv) olefin sulfates having about 12 to about 24 carbons;
(v) β-alkyloxy alkane sulfonates:
(vi) reaction products of fatty acids esterified with isethionic acid and neutralized with sodium hydroxide;
(vii) $R_1$—$SO_3$—M water-soluble salts wherein $R_1$ is a saturated aliphatic hydrocarbon radical having from about 8 to about 24 carbon atoms and M is a cation; and
(viii) mixtures thereof;

(b) from about 0.1% to about 10%, by weight, of a dispersed, insoluble, nonionic silicone hair conditioning agent comprising a non-volatile, insoluble, non-ionic silicone fluid component and a silicone resin component supplied in a nonvolatile silicone fluid, wherein the weight ratio of the nonvolatile silicone fluid component to the silicone resin component is from about 19:1 to about 400:1;

(c) from about 0.2% to about 10%, by weight, of a soluble cationic, amino or quaternary ammonium conditioning surfactant having a cationic nitrogen atom and at least one N-radical containing one or more hydrophilic moieties that are within 4 carbon atoms, inclusive, of a cationic nitrogen, said hydrophilic moieties being selected from the group consisting of alkoxy, polyoxyalkylene, alkylamido, hydroxyalkyl, and alkylester moieties, and combinations thereof; said cationic conditioning surfactant having the structure

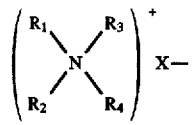

wherein $R_1$, $R_2$, $R_3$ and $R_4$ independently are substituted or un substituted hydrocarbyl chains of from 1 to about 30 carbon atoms, or a hydrocarbyl having from 1 to about 30 carbon atoms and containing one or more aromatic, ether, ester, amido, or amino moieties present as substituents or as linkages in the radical chain, and wherein
(i) at least one of the $R_1$-$R_4$ radicals contains one or more hydrophilic moieties selected from alkoxy, polyoxyalkylene, alkylamido, hydroxyalkyl, alkylester, and combinations thereof; or
(ii) two of $R_1$, $R_2$, $R_3$ and $R_4$ are covalently linked to form a ring structure, and said cationic conditioning surfactant has at least one nonionic radical containing one or more hydrophilic moieties selected from alkoxy, polyoxyalkylene, alkylamido, hydroxyalkyl, alkylester, and combinations thereof; and X is a soluble salt forming anion;

(d) an aqueous carrier, and
(e) from about 0.1% to about 20% of a detersive surfactant selected from the group consisting of nonionic, zwitterionic and amphoteric surfactants, and mixtures thereof; wherein the composition is essentially free from volatile silicone.

20. A shampoo composition as in claim 19, wherein the silicone conditioning agent is present at a level of from about 0.5% to about 5% by weight and comprises a silicone fluid component containing polydimethylsiloxane gum having a viscosity greater than about 1,000,000 centistokes, and a polydimethylsiloxane fluid having a viscosity of from about 10 centistokes to about 100,000 centistokes, wherein the weight ratio of gum to fluid is from about 30:70 to about 70:30.

21. A shampoo composition according to claim 19, wherein the anionic surfactant comprises from about 2% to about 16% by weight of alkyl sulfates and from about 0% to about 14% by weight of ethoxylated alkyl sulfates.

22. A shampoo composition according to claim 21, further comprising from about 0% to about 10% by weight of a detersive surfactant selected from the group consisting of nonionic surfactants, amphoteric surfactants, zwitterionic surfactants and mixtures thereof.

23. A liquid hair conditioning shampoo composition comprising:
(a) from about 5% to about 50%, by weight, of an anionic surfactant component selected from the group consisting of:
(i) alkyl sulfates;
(ii) ethoxylated alkyl sulfates;
(iii) succinamates;
(iv) olefin sulfates having about 12 to about 24 carbons;
(v) β-alkyloxy alkane sulfonates;
(vi) reaction products of fatty acids esterified with isethionic acid and neutralized with sodium hydroxide;
(vii) $R_1$—$SO_3$—M water-soluble salts wherein $R_1$ is a saturated aliphatic hydrocarbon radical having from about 8 to about 24 carbon atoms and M is a cation; and
(viii) mixtures thereof;

(b) from about 0.1% to about 10%, by weight, of a dispersed, insoluble, nonionic silicone hair conditioning agent comprising a non-volatile, insoluble, non-ionic silicone fluid component and a silicone resin component supplied in a nonvolatile silicone fluid, wherein the weight ratio of the nonvolatile silicone fluid component to the silicone resin component is from about 19:1 to about 400:1;

(c) from about 0.2% to about 10%, by weight, of a soluble, cationic conditioning surfactant selected from the group consisting of:

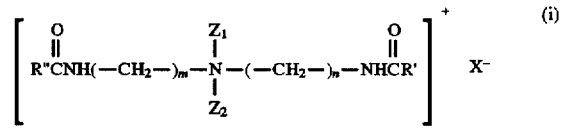

wherein $Z_1$ is a $C_1$-$C_3$ alkyl, $Z_2$ is a $C_1$-$C_3$ hydroxyalkyl, n and m independently are integers from 2 to 4, inclusive, R' and R" independently are substituted or unsubstituted hydrocarbyls, and X is a soluble salt-forming anion;

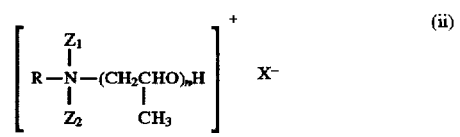

wherein R is a $C_1$-$C_3$ alkyl, $Z_1$ and $Z_2$ are, independently, $C_2$-$C_4$ alkyl or alkenyl, n is from about 2 to about 40, anti X is a soluble-salt forming anion;

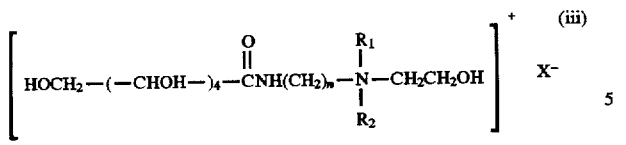

wherein n is 2 or 3, $R_1$ and $R_2$ independently are $C_1-C_3$ hydrocarbyls and X is a soluble salt-forming anion;

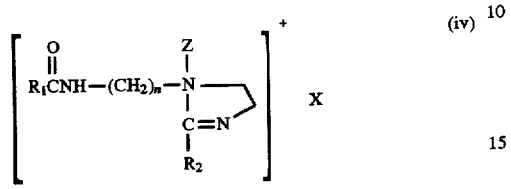

wherein $R_1$ and $R_2$, independently, are $C_{12}-C_{20}$ hydrocarbyls, Z is a $C_1-C_3$ hydrocarbyl, n is 2 or 3, and X is a soluble salt forming anion;

(v) salts of primary, secondary and tertiary fatty amines; and (vi) mixtures thereof; and (d) an aqueous carrier, where the composition is essentially free of volatile silicone.

24. A liquid hair conditioning shampoo composition comprising:

(a) from about 5% to about 50%, by weight, of an anionic surfactant component selected from the group consisting of:

(i) alkyl sulfates;

(ii) ethoxylated alkyl sulfates; and (iii) mixtures thereof;

(b) from about 0.1% to about 10%, by weight, or a dispersed, insoluble, nonionic silicone hair conditioning agent comprising a non-volatile, insoluble, nonionic silicone fluid component and a silicone resin component supplied in a nonvolatile silicone fluid, wherein the weight ratio of the nonvolatile silicone fluid component to the silicone resin component is from about 19:1 to about 400:1;

(c) from about 0.2% to about 10%, by weight, of a soluble, cationic conditioning surfactant selected from the group consisting of:

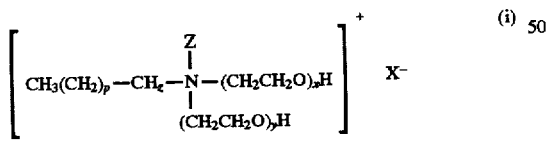

wherein n is from 8–28, x+y=2 to about 15, Z is a $C_1-C_3$ alkyl, and X is a water soluble salt forming anion;

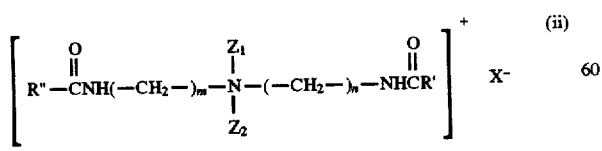

wherein $Z_1$ is a $C_1-C_3$ alkyl, $Z_2$ is a $C_1-C_3$ hydroxyalkyl, n and m independently are integers from 2 to 4, inclusive, R' and R" independently are substituted or unsubstituted hydrocarbyls, and X is a soluble salt-forming anion;

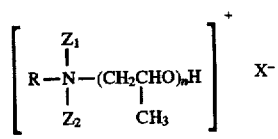

wherein R is a $C_1-C_3$ alkyl, $Z_1$ and $Z_2$ are, independently, $C_2-C_4$ alkyl or alkenyl, n is from about 2 to about 40, and X is a soluble-salt forming anion;

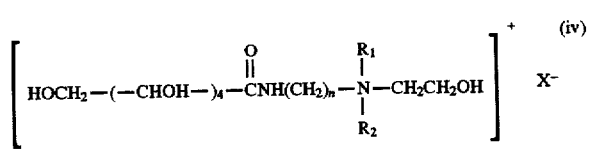

wherein n is 2 or 3, $R_1$ and $R_2$ independently are $C_1-C_3$ hydrocarbyls and X is a soluble salt-forming anion; and (d) from about 0.1% to about 20% of a detersive surfactant selected from the group consisting of nonionic, zwitterionic, amphoteric surfactants, and mixtures thereof; and (e) an aqueous carrier, wherein the composition is essentially free of volatile silicone.

25. A composition according to claim 24 comprising:

a(i) from about 2% to about 16% alkyl sulfate; and a(ii) from about 0% to about 14% ethoxylated alkyl sulfate; wherein the total detersive surfactant level is from about 10% to about 25%.

26. A composition according to claim 24 wherein the detersive surfactant selected from the group consisting of nonionic, zwitterionic, and amphoteric surfactants thereof is selected from the group consisting of:

(i) condensation products of ethylene oxide with alkyl phenols having an alkyl group containing from about 6 to about 20 carbon atoms;

(ii) condensation products of ethylene oxide with hydrophobic bases formed by a reaction of propylene oxide and ethylene diamine;

(iii) condensation products of ethylene oxide with aliphatic alcohols having from about 8 to about 18 carbon atoms;

(iv) long chain tertiary amine oxides;

(v) long chain tertiary phosphine oxides;

(vi) long chain dialkyl sulfoxides;

(vii) compounds of the formula:

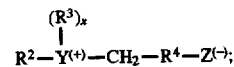

wherein $R^2$ has an alkyl, alkenyl, or hydroxy alkyl radical having from about 8 to about 18 carbon atoms, from 0 to about 10 ethylene oxide moieties, and from 0 to about 1 glyceryl moiety;

Y is selected from the group consisting of nitrogen, phosphorus, and sulfur;

$R^3$ is an alkyl or monohydroxyalkyl group having from about 1 to about 3 carbon atoms;

$R^4$ is an alkylene or hydroxyalkylene of from about 1 to about 4 carbon atoms;

Z is a radical selected from the group consisting of carboxylate, sulfonate, sulfate, phosphonate, and phosphate groups; and X is 1 when Y is sulfur, and 2 when Y is nitrogen or phosphorus;

(viii) betaines;

(ix) sulfobetaines;

(x) substituted aliphatic secondary and tertiary amines having aliphatic substituents wherein one of the aliphatic substituents has from about 8 to about 18 carbon atoms, and one of the aliphatic substituents has an anionic water solubilizing group selected from the group consisting of carboxyl, sulfonate, sulfate, phosphate, phosphonate, and mixtures thereof; and (xi) mixtures thereof.

27. A composition according to claim 1 wherein the silicone resin has a ratio of oxygen:silicon atoms of at least about 1.2:1.0.

28. A composition according to claim 27 wherein the weight ratio of the nonvolatile silicone fluid component to the silicone resin component is from about 19:1 to about 100:1.

29. A composition according to claim 19 wherein the silicone resin has a ratio of oxygen:silicon atoms of at least about 1.2:1.0.

30. A composition according to claim 29 wherein the silicone resin has an average molecular weight of from about 1000 to about 10,000, and a M:Q ratio of from about 0.5:1.0 to about 1.5:1.0.

31. A liquid hair conditioning shampoo composition comprising:

(a) from about 5% to about 50%, by weight, of an anionic surfactant component selected from the group consisting of:

(i) alkyl sulfates;

(ii) ethoxylated alkyl sulfates;

(iii) succinamates;

(iv) olefin sulfates having about 12 to about 24 carbons;

(v) β-alkyloxy alkane sulfonates;

(vi) reaction products of fatty acids esterified with isethionic acid and neutralized with sodium hydroxide;

(vii) $R_1$—$SO_3$—M water-soluble salts wherein $R_1$ is a saturated aliphatic hydrocarbon radical having from about 8 to about 24 carbon atoms and M is a cation; and (viii) mixtures thereof;

(b) from about 0.1% to about 10%, by weight, of a dispersed, insoluble, nonionic silicone hair conditioning agent comprising a non-volatile, insoluble, nonionic silicone fluid component and a silicone resin component supplied in a nonvolatile silicone fluid wherein the weight ratio of the nonvolatile silicone fluid component to the silicone resin component is from about 19:1 to about 400:1

(c) from about 0.2% to about 10%, by weight, of a soluble cationic conditioning surfactant of the formula:

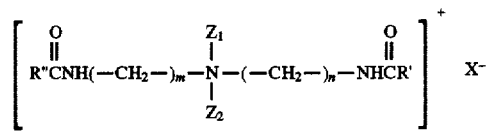

wherein $Z_1$ and $Z_2$ independently are substituted or unsubstituted hydrocarbyls, n and m independently are integers from 2 to 4, R' and R" independently are substituted or unsubstituted hydrocarbyls, and X is a soluble salt-forming anion;

(d) an aqueous carrier; and (e) from about 0.1% to about 5% of an additional cationic component, said additional cationic component being an anionic surfactant compatible, cationic anti-static agent comprising tricetyl methyl ammonium salt, wherein the composition is essentially free of volatile silicone.

32. A liquid hair conditioning composition as in claim 31, wherein $Z_1$ is a $C_1$–$C_3$ alkyl, $Z_2$ is a hydroxyethyl or hydroxymethyl, m and n independently are 2 and R' and R" independently are $C_{12}$–$C_{20}$ alkyl or alkenyl.

* * * * *